US012586278B2

(12) United States Patent
Siegel et al.

(10) Patent No.: US 12,586,278 B2
(45) Date of Patent: Mar. 24, 2026

(54) AI-DRIVEN PET RECONSTRUCTION FROM HISTOIMAGE

(71) Applicant: Siemens Medical Solutions USA, Inc., Malvern, PA (US)

(72) Inventors: Stefan Siegel, Knoxville, TN (US); Inki Hong, Knoxville, TN (US); Ziad Burbar, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 279 days.

(21) Appl. No.: 18/610,566

(22) Filed: Mar. 20, 2024

(65) Prior Publication Data

US 2025/0299391 A1     Sep. 25, 2025

(51) Int. Cl.
| | |
|---|---|
| *G06T 12/30* | (2026.01) |
| *A61B 6/00* | (2006.01) |
| *A61B 6/03* | (2006.01) |
| *G06T 7/00* | (2017.01) |
| *G06T 9/00* | (2006.01) |

(52) U.S. Cl.
CPC .............. *G06T 12/30* (2026.01); *A61B 6/037* (2013.01); *A61B 6/5282* (2013.01); *G06T 7/0012* (2013.01); *G06T 9/00* (2013.01); *G06T 2207/10104* (2013.01); *G06T 2207/20084* (2013.01)

(58) Field of Classification Search
CPC ......... G06T 12/30; G06T 7/0012; G06T 9/00; G06T 2207/10104; G06T 2207/20084; G06T 12/10; G06T 2211/441; A61B 6/037; A61B 6/5282; A61B 6/5211
See application file for complete search history.

(56) References Cited

U.S. PATENT DOCUMENTS

| | | | | |
|---|---|---|---|---|
| 2003/0004405 A1* | 1/2003 | Townsend | .............. | A61B 6/463 |
| | | | | 600/407 |
| 2009/0110256 A1* | 4/2009 | Thielemans | ......... | A61B 6/5235 |
| | | | | 382/131 |
| 2013/0101193 A1* | 4/2013 | Ra | ........................... | G06T 12/10 |
| | | | | 382/131 |
| 2019/0130569 A1* | 5/2019 | Liu | ......................... | G06T 12/30 |
| 2019/0355159 A1* | 11/2019 | Bai | ......................... | H04W 8/14 |
| 2020/0211236 A1* | 7/2020 | Zhang | .................... | G06N 3/084 |
| 2021/0065412 A1* | 3/2021 | Feng | ..................... | A61B 6/037 |

(Continued)

OTHER PUBLICATIONS

Whiteley et al., "FastPET: Near Real-Time PET Reconstruction from Histo-Images Using a Neural Network"; IEEE (Year: 2020).*

(Continued)

*Primary Examiner* — Aaron W Carter

(57) ABSTRACT

Systems and methods include acquisition of a computed tomography image of an object, determination of a linear attenuation coefficient map based on the computed tomography image, acquisition of positron emission tomography (PET) data of the object, determination of a histoimage of the object based on the PET data, determination of a scatter histoimage based on the histoimage and the linear attenuation coefficient map, determination of a scatter-corrected histoimage based on the histoimage and the scatter histo-image, and input of the computed tomography image and the scatter-corrected histoimage to a trained neural network to generate a PET image.

20 Claims, 7 Drawing Sheets

(56) References Cited

U.S. PATENT DOCUMENTS

| | | | |
|---|---|---|---|
| 2021/0104079 A1* | 4/2021 | Whiteley | A61B 6/037 |
| 2021/0282732 A1* | 9/2021 | Qi | A61B 6/5235 |
| 2022/0091286 A1* | 3/2022 | Panin | A61B 6/037 |
| 2023/0206516 A1* | 6/2023 | Qi | G06T 12/10 |
| | | | 382/131 |
| 2024/0153166 A1* | 5/2024 | He | G06T 12/10 |
| 2024/0242398 A1* | 7/2024 | Xi | G06N 3/045 |
| 2025/0045937 A1* | 2/2025 | Sun | G06T 7/30 |
| 2025/0148662 A1* | 5/2025 | Bharkhada | G06T 12/20 |
| 2025/0259349 A1* | 8/2025 | Panin | G06T 12/10 |
| 2025/0265715 A1* | 8/2025 | Zuehlsdorff | G06T 7/0014 |
| 2025/0299391 A1* | 9/2025 | Siegel | G06T 12/30 |
| 2025/0322564 A1* | 10/2025 | Mehranian | G06T 12/10 |

OTHER PUBLICATIONS

Li et al., "Deep Learning Accelerates Accurate Scatter Correction with Histo-image in TOF PET/CT System", IEEE (Year: 2022).*

* cited by examiner

200

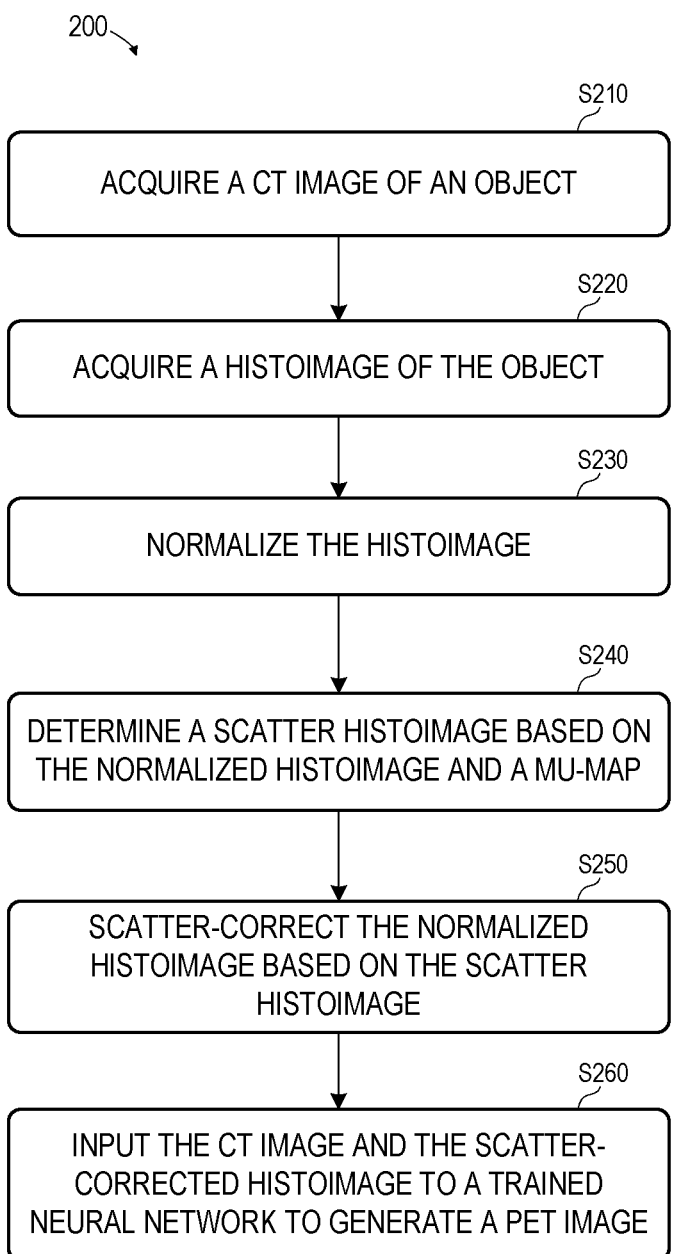

S210

ACQUIRE A CT IMAGE OF AN OBJECT

S220

ACQUIRE A HISTOIMAGE OF THE OBJECT

S230

NORMALIZE THE HISTOIMAGE

S240

DETERMINE A SCATTER HISTOIMAGE BASED ON THE NORMALIZED HISTOIMAGE AND A MU-MAP

S250

SCATTER-CORRECT THE NORMALIZED HISTOIMAGE BASED ON THE SCATTER HISTOIMAGE

S260

INPUT THE CT IMAGE AND THE SCATTER-CORRECTED HISTOIMAGE TO A TRAINED NEURAL NETWORK TO GENERATE A PET IMAGE

*FIG. 2*

700
710
712
715
716
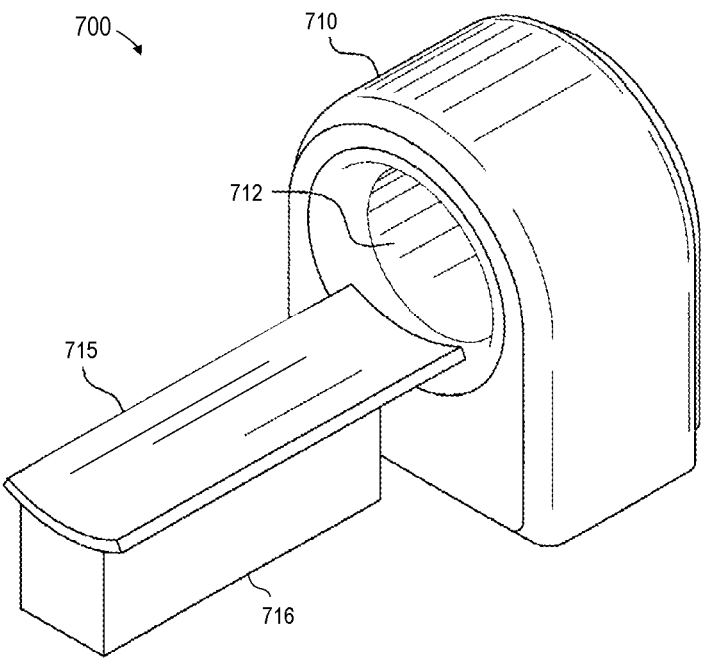
730
731   CONTROL PROGRAM
732   SCATTER HISTOIMAGE NETWORK
733   PET RECONSTRUCTION NETWORK
734   CT IMAGES
735   PET IMAGES
723   PET SYSTEM INTERFACE
724   CT SYSTEM INTERFACE
725   BED INTERFACE
722   PROCESSING UNIT(S)
726   TERMINAL INTERFACE
720
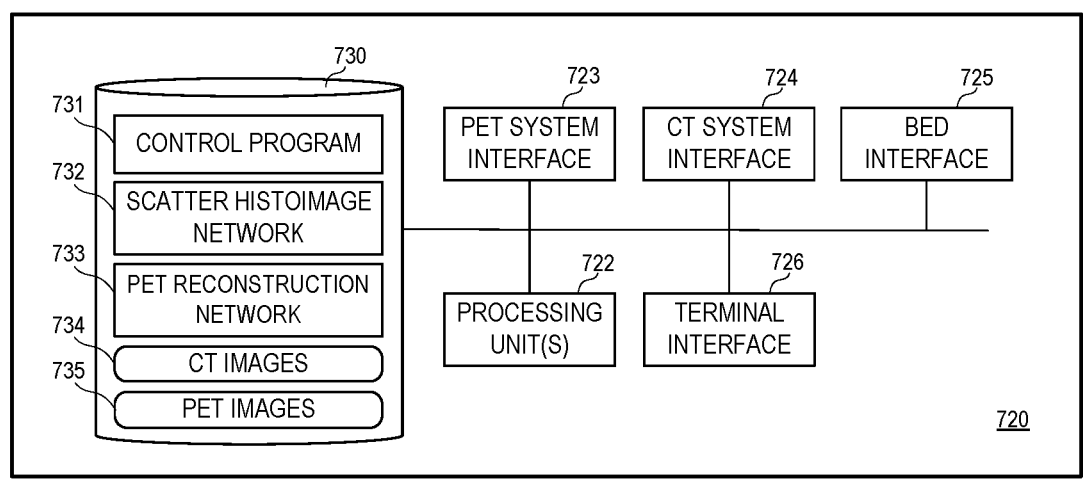
740
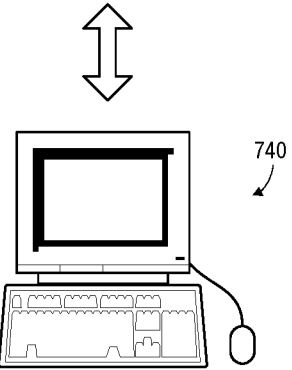
*FIG. 7*

AI-DRIVEN PET RECONSTRUCTION FROM HISTOIMAGE

BACKGROUND

Positron Emission Tomography (PET) generates functional images which represent biological processes (e.g., glucose metabolism, receptor affinity) occurring within a patient. According to PET techniques, a radiotracer is administered to a patient via intravenous injection, inhalation, oral ingestion or direct organ injection. Radioactive decay of the tracer as it travels within the patient generates positrons which eventually encounter electrons and are annihilated thereby.

An annihilation produces two 511 keV photons which travel in approximately opposite directions. A coincidence is identified when two detector crystals detect the arrival of two photons within a short time window indicating that the two photons arose from the same positron annihilation. Because the two "coincident" photons travel in approximately opposite directions, the locations of the two detector crystals determine a Line-of-Response (LoR) along which an annihilation may have occurred. PET data represents each detected annihilation as a LoR between two detector crystals.

An image is reconstructed from the PET data using known algorithms such as filtered backprojection (FBP) and ordered subsets expectation maximization (OSEM). PET image reconstruction is complex, resource-intensive and time-consuming. For example, reconstruction usually includes determination and subtraction of random coincidences and scatter coincidences from the PET data, attenuation correction, motion correction, correction for system sensitivity, and other suitable steps.

Developments in PET scanner technology have exacerbated the difficulties of PET image reconstruction. Long axial field-of-view scanners and smaller detector crystals (i.e., finer sampling) have independently increased the number of LoRs as well as the complexity of the corrections. In addition, dynamic workflow techniques have placed greater demands on the speed and quality of image reconstruction.

These challenges are currently managed by reducing (i.e., mashing) the PET data, modifying reconstruction algorithms to compromise image quality characteristics such as spatial resolution and noise, and/or using more powerful processing hardware with associated increases in memory requirements. This hardware is expensive, consumes significant power and generates significant heat. Moreover, these remedial approaches are not infinitely scalable.

Systems are desired to reconstruct suitable PET images in a resource-efficient manner.

BRIEF DESCRIPTION OF THE DRAWINGS

FIG. 2 is a flow diagram of a process to generate a corrected PET image according to some embodiments.

FIG. 7 is a block diagram of an imaging system according to some embodiments.

DETAILED DESCRIPTION

The following description is provided to enable any person in the art to make and use the described embodiments. Various modifications, however, will remain apparent to those in the art.

Embodiments utilize a trained neural network to derive a PET image from a normalized PET histoimage and a corresponding anatomical image. Embodiments may thereby generate fully-corrected, low-noise, high spatial resolution PET images in a practical timeframe using typically-available computing resources.

A PET histoimage is a simple backprojection of each detected annihilation with Time-of-Flight (ToF) localization along an LoR. Briefly, list-mode data is acquired and normalized based on scanner sensitivity. The list-mode data may also be attenuation-corrected based on previously-acquired anatomical information. A normalized PET histoimage is generated from the normalized list-mode data. A scatter histoimage is generated based on the PET histoimage and a corresponding mu-map, and the scatter histoimage is used to scatter-correct the PET histoimage. The scatter-corrected PET histoimage and an anatomical image (e.g., a Computed Tomography (CT) image) are then input to a trained neural network to generate a corrected PET image.

Figure 1:
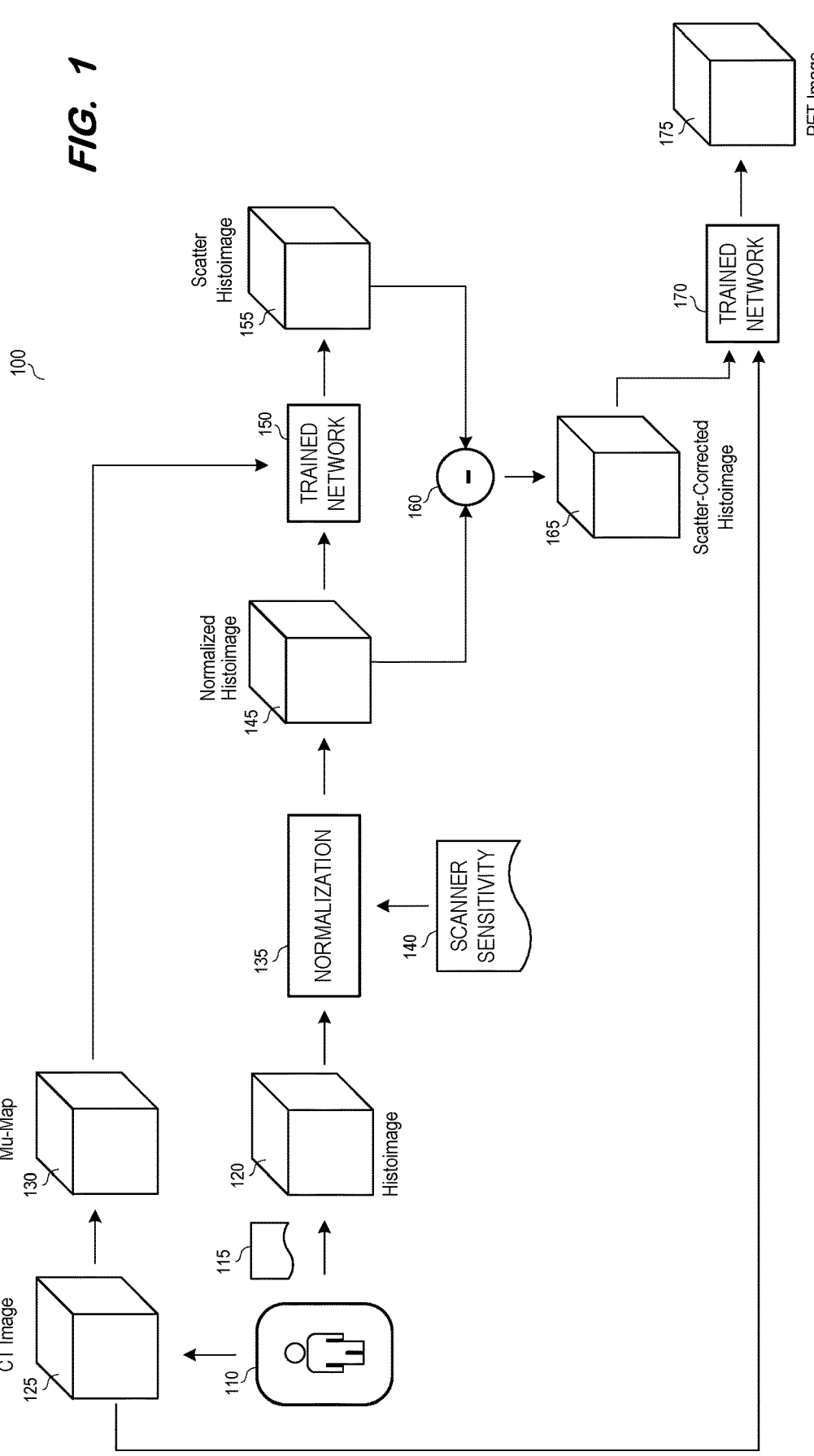
FIG. 1 is a block diagram of a system to generate a corrected PET image according to some embodiments.

FIG. 1 is a block diagram of system 100 to generate a corrected PET image according to some embodiments. The illustrated components of system 100 may be implemented in computer hardware, in program code and/or in one or more computing systems executing such program code as is known in the art. Such a computing system may include one or more processing units which execute program code stored in a memory system. More than one functional component may be implemented by a single computing system in some embodiments. One or more of the computing systems may comprise a virtual machine, and one-or more computing systems may comprise a cloud-based compute resource providing on-demand scalability and failure recovery.

Scanner 110 may comprise a PET/CT scanner capable of generating PET data 115 using any suitable PET imaging protocol. For each detected annihilation, PET data 115 provides the locations of the two detector crystals which detected the photons of the annihilation (i.e., and which define an LoR along which the annihilation occurred), the time at which each photon of the annihilation reached each detector crystal and the difference between the arrival times of the two photons at the detector crystals (i.e., ToF data). The ToF data is used to estimate the position along the LoR at which the annihilation occurred.

Histoimage 120 is generated from PET data 115. Histoimage 120 includes a three-dimensional image coordinate for each annihilation represented in PET data. The coordinate is along the LoR of the annihilation, at a point determined by the ToF data of the annihilation. For example, the point is at the midpoint of the LoR if the photons of the annihilation were detected at a same time but is closer to one detector if the one detector detected its photon before the other detector detected its photon. In this regard, a histoimage may be considered an imprecise estimate of a reconstructed tomographic image.

Scanner 110 also generates three-dimensional CT image 125 of the patient using any suitable CT imaging protocol.

Scanner 110 may generate CT image 125 substantially contemporaneously with the acquisition of PET data 115. For example, a PET imaging system of scanner 110 may be operated to acquire PET data 115 while a patient lies in a given position on a bed of scanner 110, and a CT imaging system of scanner 110 may be operated shortly thereafter to acquire CT data 125 while the patient remains on the bed in the given position. Since the geometric transformation (if any) between coordinates of the PET imaging system and the CT imaging system is known, resulting images may be easily registered with one another.

Linear Attenuation Coefficient (LAC) map ("mu-map") 130 is derived from CT image 125 as is known in the art. A mu-map provides attenuation coefficients of the subject tissue and is typically used for attenuation correction of emission data such as PET data and single-photon-emission-computer-tomography (SPECT) data.

Normalization component 135 generates normalized histoimage 145 based on histoimage 120 and scanner sensitivity data 140. Scanner sensitivity data 140 may specify the sensitivity of scanner 110 at various locations within the field-of-view of scanner 110. In some embodiments, the most-sensitive location of scanner 110 is specified to exhibit a sensitivity of 1.0 while other locations exhibit lower sensitivities. Normalization component 135 may account for such sensitivities by dividing histoimage 120 by the location-specific sensitivities of data 140 as is known in the art.

Normalization component 135 may also perform attenuation correction on histoimage 120 based on mu-map 130. Normalized histoimage 145 may therefore be a sensitivity- and attenuation-corrected version of histoimage 120. Some embodiments may omit the sensitivity-correction and/or the attenuation correction of histoimage 120.

Normalized histoimage 145 and mu-map 130 are input to trained network 150 to generate scatter histoimage 155. In this regard, trained network 150 has been trained to estimate the scatter coincidences of normalized histoimage 145. Network 150 may comprise hardware and software for executing a mapping defined by a specified neural network architecture and trained network parameters. According to some embodiments, scatter histoimage 155 is generated from normalized histoimage 145 and mu-map 130 using algorithms rather than a trained neural network.

Scatter histoimage 155 exhibits the same size as normalized histoimage 145. According to some embodiments, normalized histoimage 145 and mu-map 130 are reduced in size prior to input to network 150, resulting in a similarly reduced-size scatter histoimage 155. The reduction of normalized histoimage 145 and mu-map 130 may comprise spatial down-sampling to a resolution which is lower than the resolution of histoimage 120.

Reduction in the size of histoimage 145 and mu-map 130 reduces the amount of data input to trained network 150, thereby increasing the efficiency of operation of network 150. Moreover, the present inventors have discovered that, because scatter is a low-frequency and source distribution-dependent phenomena, an accurate scatter histoimage may be generated from a significantly-reduced histoimage.

Scatter correction component 160 generates scatter-corrected histoimage 165 based on normalized histoimage 145 and scatter histoimage 155. According to some embodiments, scatter correction component 160 subtracts scatter histoimage 155 from normalized histoimage 145 to generate scatter-corrected histoimage 165.

Scatter-corrected histoimage 165 and CT image 125 are input to trained network 170 to generate PET image 175. In contrast to existing approaches, PET image 175 may exhibit improved signal-to-noise ratio (SNR), spatial resolution and scatter correction, while requiring fewer computing resources. If normalized histoimage 145 and scatter histoimage 155 are of reduced resolution with respect to histoimage 120, scatter-corrected histoimage 165 is expanded to the size of histoimage 120 prior to input to network 170. The parameters of network 170 may be trained as described below, and network 170 may comprise any hardware and software for executing a mapping defined by a specified neural network architecture and trained network parameters.

The examples provided herein are directed to PET imaging, but embodiments are not limited thereto. For example, anatomical image data is described herein as being acquired using CT imaging but may be acquired using MR imaging, with any required mu-map being generated from MR data. Embodiments may be implemented using other MI modalities including SPECT imaging.

FIG. 2 is a flow diagram of process 200 to generate a corrected PET image according to some embodiments. Process 200 may be performed by any combination of hardware and software that is or becomes known. Program code embodying processes described herein may be stored by any non-transitory tangible medium, including a fixed disk, a volatile or non-volatile random-access memory, a DVD, a Flash drive, and a magnetic tape, and executed by any suitable processing unit, including but not limited to one or more microprocessors, microcontrollers, processor cores, and processor threads. Embodiments are not limited to the examples described below.

A CT image of an object is acquired at S210 using any suitable CT imaging protocol. Next, at S220, a histoimage of the object is acquired. Acquisition of the histoimage may include operating a PET scanner to acquire PET data of the object and generating the histoimage from the PET data.

The histoimage is normalized at S230. The histoimage may be normalized to account for spatial sensitivity of the PET scanner. Normalization at S230 may also include attenuation correction based on a mu-map derived from the acquired CT image. The normalized histoimage may also be compressed at S230 to reduce the amount of data used to represent the normalized histoimage.

A scatter histoimage is determined based on the normalized histoimage and the mu-map at S240. According to some embodiments, the normalized histoimage and the mu-map are input to a trained neural network at S240 to generate the scatter histoimage. In other embodiments, the scatter histoimage is generated from the normalized histoimage and the mu-map using known algorithms.

Figure 3:
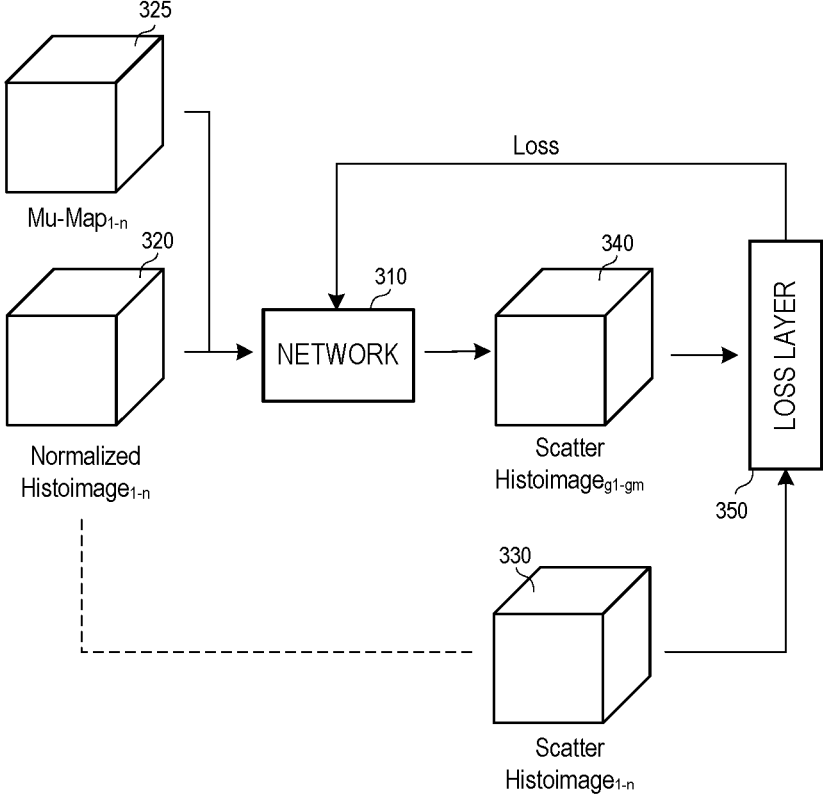
FIG. 3 illustrates training of a neural network to generate a scatter histoimage based on a normalized histoimage according to some embodiments.

FIG. 3 illustrates training of neural network 310 to generate a scatter histoimage based on a normalized histoimage and a mu-map at S240 according to some embodiments. Network 310 is shown as a supervised learning-compatible network. Network 310 may comprise any type of supervised or unsupervised learning-compatible network, algorithm, decision tree, etc. to receive image data and to output image data that is or becomes known. For example, network 310 may comprise a generator of a Generative Adversarial Network (GAN) having trainable parameters as is known in the art.

Network 310 may comprise a plurality of layers of neurons which receive input, change internal state according to that input, and produce output depending on the input and internal state. The output of certain neurons is connected to the input of other neurons to form a directed and weighted graph. The weights as well as the functions that compute the internal states are iteratively modified during training. Thusly-trained network 310 may be implemented by a set of linear equations, executable program code, a set of hyper-parameters defining a model structure and a set of corresponding weights, or any other representation of the mapping of input to output which was learned as a result of the training.

The training data of FIG. 3 consists of N normalized histoimages 320, N mu-maps 325 and N corresponding scatter histoimages 330. Each of the N pairs of normalized histoimages 320 and N mu-maps 325 may be generated as described above with respect to FIG. 1, albeit using different patients and different PET scanners. Each of N normalized histoimages 320 may be attenuation-corrected, sensitivity-corrected and/or compressed in the same manner as will be applied to normalized histoimages which will be input to network 310 during deployment thereof.

Each "ground truth" scatter histoimage 330 is generated from a respective pair of normalized histoimages 320 and mu-maps 325. Generation of scatter histoimages 330 may utilize any one or more techniques that are or become known, including but not limited to single scatter simulation, phantom-based techniques, and data simulation. In some embodiments, generation of a scatter histoimage 330 is also based on the PET data underlying its corresponding normalized histoimage 320.

Figure 4:
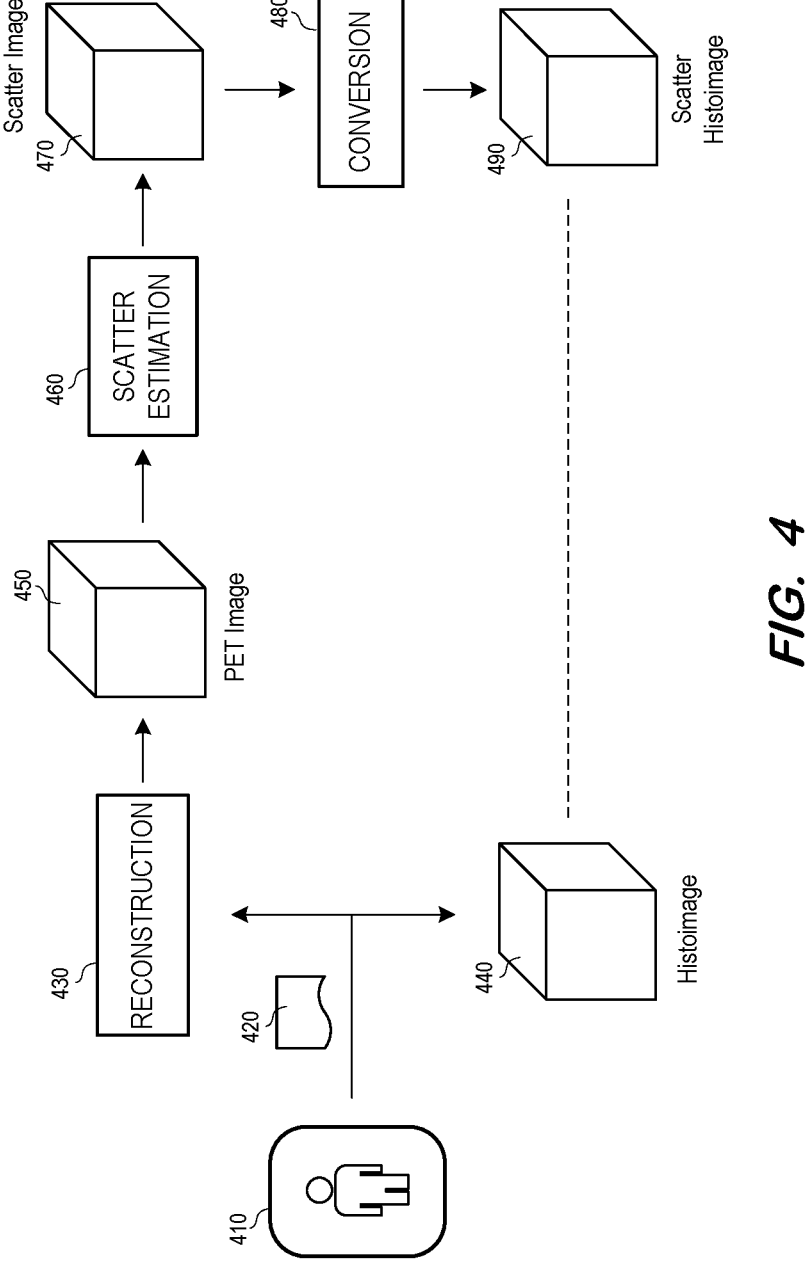
FIG. 4 illustrates generation of neural network training data according to some embodiments.

FIG. 4 illustrates generation of a histoimage and a corresponding scatter histoimage for use in training a network according to some embodiments. Scanner 410 generates PET data 420 of a patient, which is converted to histoimage 440 and used by reconstruction component 430 to reconstruct PET image 450. Histoimage 440 may be normalized based on sensitivity of scanner 410 and/or attenuation-corrected. Similarly, reconstruction component 430 may apply sensitivity correction and/or attenuation correction during reconstruction of PET image 450.

Scatter estimation component 460 generates scatter image 470 based on PET image 450 using any algorithm that is or becomes known. In some embodiments, component 460 operates directly on PET data 420 to generate scatter image 470. Conversion component 480 converts scatter image 470 to scatter histoimage 490. Conversion component 480 may convert scatter image 470 to list-mode data and generate scatter histoimage 490 therefrom as described above. Histoimage 440 and scatter histoimage 490 may be used as corresponding input data and ground truth data during training of a network as described below.

As described above, a scatter correction component may scatter-correct the normalized histoimage by subtracting the scatter histoimage from the normalized histoimage at S250. The scatter-corrected histoimage and the acquired CT image may then be input to a trained network to generate a PET image at S260.

Figure 5:
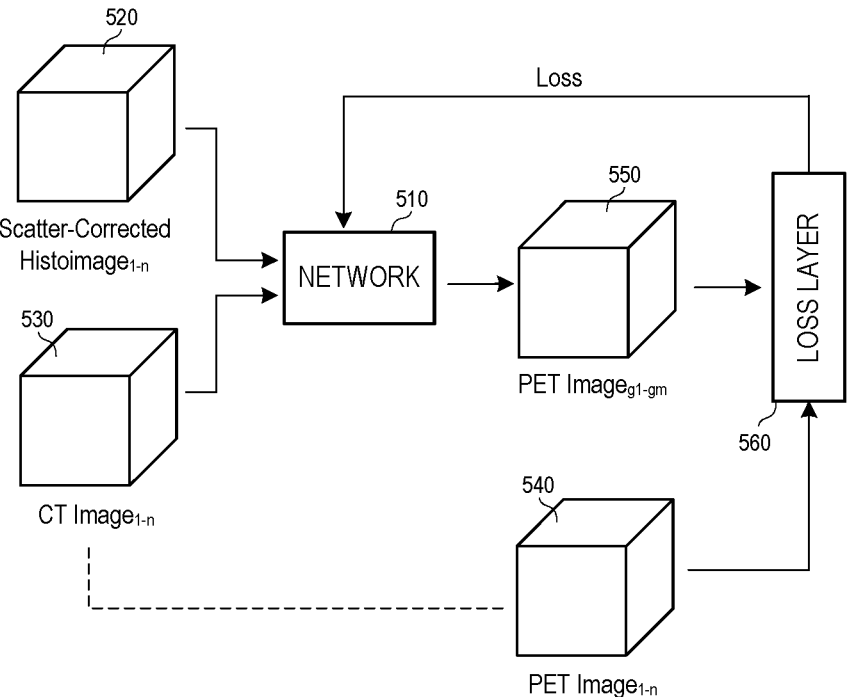
FIG. 5 illustrates training of a neural network to generate a corrected PET image based on a CT image and a corrected histoimage according to some embodiments.

FIG. 5 illustrates training of neural network 510 to generate a PET histoimage based on a scatter-corrected histoimage and an anatomical image according to some embodiments. Network 510 is shown as a supervised learning-compatible network but comprise any type of supervised or unsupervised learning-compatible system as described above with respect to network 310.

Figure 6:
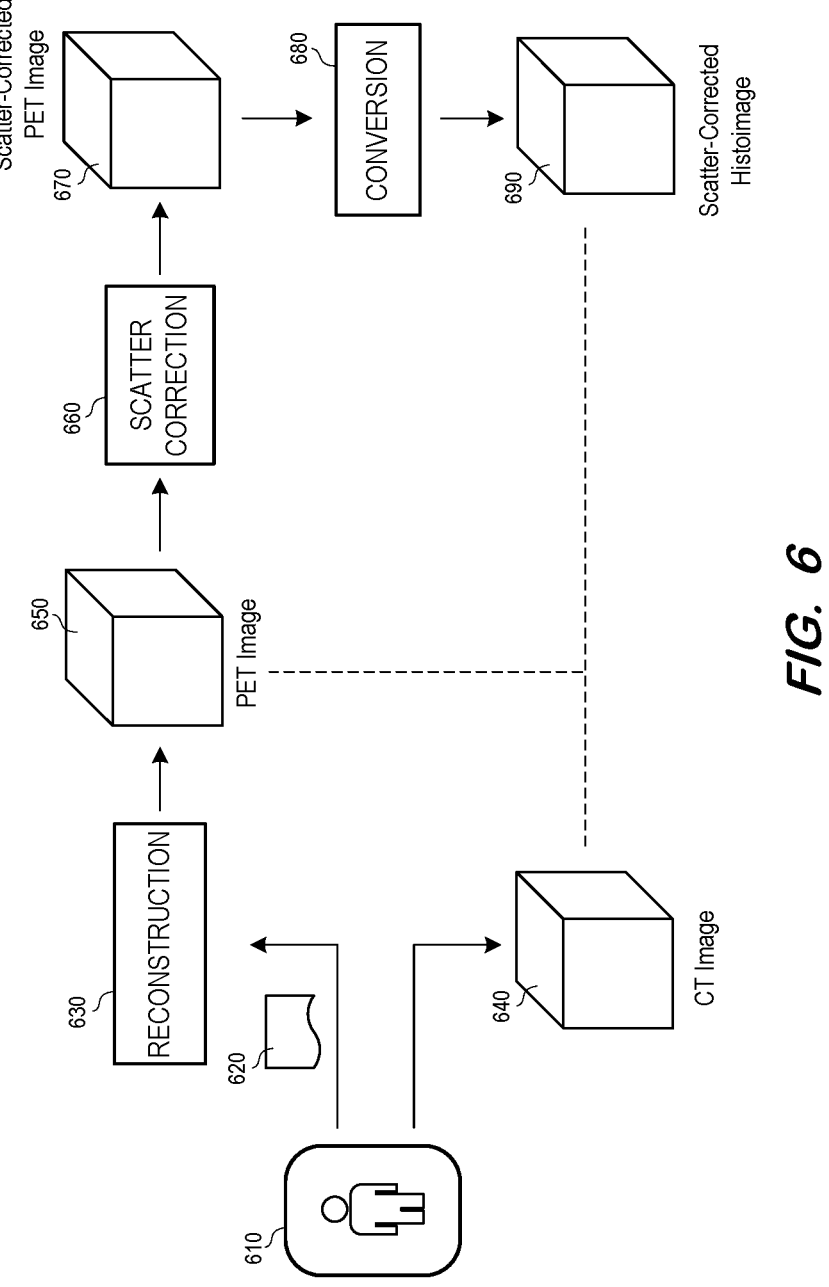
FIG. 6 illustrates generation of neural network training data according to some embodiments.

FIG. 6 illustrates generation of a scatter-corrected histoimage, an anatomical image and a corresponding PET histoimage for use in training a network according to some embodiments. Scanner 610 generates PET data 620 of a patient and contemporaneously generates CT image 640. Reconstruction component 630 reconstructs PET image 650 from PET data 620. PET image 650 may be attenuation-corrected based on attenuation data derived from CT image 640.

Scatter correction component 660 generates scatter-corrected PET image 670 based on PET image 650 using any scatter-correction algorithm that is or becomes known. Conversion component 680 then converts scatter-corrected PET image 670 to scatter-corrected histoimage 690. Conversion component 680 may convert scatter-corrected PET image 670 to list-mode data and generate scatter-corrected histoimage 490 therefrom in some embodiments. CT image 640 and scatter-corrected histoimage 670 may be used as input data and scatter-corrected PET image 670 may be used as corresponding ground truth data during training of a network as shown in FIG. 5.

A batch of M scatter-corrected histoimages 520 and a batch M of CT images 530 are input to network 510 during training. Network 510 generates a PET image 550 for each pair of scatter-corrected histoimages 520 and CT images 530 of the batch. Loss layer 560 calculates a loss based on differences between each of the M generated PET images 550 and its corresponding ground truth PET image 540. The loss is back-propagated to network 510, which is modified to minimize the loss. Additional batches are input and network 510 is modified accordingly until training is determined to be complete.

FIG. 7 illustrates PET/CT scanner 700 to execute one or more of the processes described herein. Embodiments are not limited to scanner 700 or to a multi-modality imaging system.

Scanner 700 includes gantry 710 defining bore 712. As is known in the art, gantry 710 houses PET imaging components for acquiring PET image data and CT imaging components for acquiring CT image data. The CT imaging components may include one or more x-ray tubes and one or more corresponding x-ray detectors as is known in the art. The PET imaging components may include any number or type of detectors including background radiation-emitting crystals and disposed in any configuration as is known in the art.

Bed 715 and base 716 are operable to move a patient lying on bed 715 into and out of bore 712 before, during and after imaging. In some embodiments, bed 715 is configured to translate over base 716 and, in other embodiments, base 716 is movable along with or alternatively from bed 715.

Movement of a patient into and out of bore 712 may allow scanning of the patient using the CT imaging elements and the PET imaging elements of gantry 710. Bed 715 and base 716 may provide continuous bed motion and/or step-and-shoot motion during such scanning according to some embodiments.

Control system 720 may comprise any general-purpose or dedicated computing system. Accordingly, control system 720 includes one or more processing units 722 configured to execute program code to cause system 720 to acquire image data and generate images therefrom, and storage device 730 for storing the program code. Storage device 730 may comprise one or more fixed disks, solid-state random-access memory, and/or removable media (e.g., a thumb drive) mounted in a corresponding interface (e.g., a Universal Serial Bus port).

Storage device 730 stores program code of control program 731. One or more processing units 722 may execute control program 731 to control CT imaging elements of scanner 700 using CT system interface 724 and bed interface 725 to acquire CT data and to reconstruct CT images 734 therefrom.

One or more processing units 722 may execute control program 731 to, in conjunction with PET system interface 723 and bed interface 725, control hardware elements to inject a radiopharmaceutical into a patient, move the patient into bore 712 past PET detectors of gantry 710, and detect photons emitted from the patient based on pulses generated by the PET detectors. The detected photons may be recorded as PET data, which may be converted to a histogram as described above.

Scatter histogram network 732 may execute based on trained network parameters to generate a scatter histoimage based on the histoimage. The histoimage may be normalized and/or compressed prior to input to scatter histoimage network 732. A scatter-corrected histoimage is then determined based on the histoimage and the scatter histoimage.

PET reconstruction network 733 is executed to generate a PET image based on a scatter-corrected histoimage and a CT image. The PET image may be saved in PET images 735. PET images 735 and CT images 734 may be transmitted to terminal 740 via terminal interface 726. Terminal 740 may comprise a display device and an input device coupled to system 720. Terminal 740 may display the received PET images 735 and CT images 733. Terminal 740 may receive user input for controlling display of the data, operation of scanner 700, and/or the processing described herein. In some embodiments, terminal 740 is a separate computing device such as, but not limited to, a desktop computer, a laptop computer, a tablet computer, and a smartphone.

Each component of scanner 700 may include other elements which are necessary for the operation thereof, as well as additional elements for providing functions other than those described herein. Each functional component described herein may be implemented in computer hardware, in program code and/or in one or more computing systems executing such program code as is known in the art. Such a computing system may include one or more processing units which execute processor-executable program code stored in a memory system.

Those in the art will appreciate that various adaptations and modifications of the above-described embodiments can be configured without departing from the claims. Therefore, it is to be understood that the claims may be practiced other than as specifically described herein.

What is claimed is:

1. A positron emission tomography (PET) scanner comprising:
 a plurality of photon detectors; and
 a processing unit to:
  determine an anatomical image of an object;
  determine a linear attenuation coefficient map based on the anatomical image;
  acquire PET data of the object at the plurality of photon detectors;
  determine a histoimage of the object based on the PET data;
  determine a scatter histoimage based on the histoimage and the linear attenuation coefficient map;
  determine a scatter-corrected histoimage based on the histoimage and the scatter histoimage; and
  input the anatomical image and the scatter-corrected histoimage to a trained neural network to generate a PET image; and
 a display to present the PET image.

2. A scanner according to claim 1, wherein determination of the scatter histoimage comprises:
 compressing of the histoimage and of the linear attenuation coefficient map; and
 determination of the scatter histoimage based on the compressed histoimage and the compressed linear attenuation coefficient map.

3. A scanner according to claim 2, wherein determination of the scatter histoimage comprises inputting of the compressed histoimage and the compressed linear attenuation coefficient map to a second trained neural network to generate the scatter histoimage.

4. A scanner according to claim 2, wherein determination of the scatter-corrected histoimage is based on the compressed histoimage and the scatter histoimage.

5. A scanner according to claim 1, wherein determination of the histoimage of the object comprises normalization of the histoimage based on a sensitivity of the scanner to determine a normalized histoimage,
 wherein the scatter histoimage is determined based on the normalized histoimage, and
 wherein the scatter-corrected histoimage is determined based on the normalized histoimage and the scatter histoimage.

6. A scanner according to claim 5, wherein determination of the scatter histoimage comprises:
 compressing of the normalized histoimage and of the compressed linear attenuation coefficient map; and
 determination of the scatter histoimage based on the compressed normalized histoimage and the compressed linear attenuation coefficient map.

7. A scanner according to claim 6, wherein determination of the scatter histoimage comprises inputting of the compressed normalized histoimage and the compressed linear attenuation coefficient map to a second trained neural network to generate the scatter histoimage.

8. A method comprising:
 acquiring a computed tomography image of an object;
 determining a linear attenuation coefficient map based on the computed tomography image;
 acquiring positron emission tomography (PET) data of the object;
 determining a histoimage of the object based on the PET data;
 determining a scatter histoimage based on the histoimage and the linear attenuation coefficient map;
 determining a scatter-corrected histoimage based on the histoimage and the scatter histoimage;
 inputting the computed tomography image and the scatter-corrected histoimage to a trained neural network to generate a PET image; and
 presenting the PET image.

9. A method according to claim 8, wherein determining the scatter histoimage comprises:
 compressing the histoimage and the linear attenuation coefficient map; and
 determining the scatter histoimage based on the compressed histoimage and the compressed linear attenuation coefficient map.

10. A method according to claim 9, wherein determining the scatter histoimage comprises inputting the compressed histoimage and the compressed linear attenuation coefficient map to a second trained neural network to generate the scatter histoimage.

11. A method according to claim 9, wherein the scatter-corrected histoimage is determined based on the compressed histoimage and the scatter histoimage.

12. A method according to claim 8, wherein determining the histoimage of the object comprises normalizing the histoimage based on a sensitivity of the scanner to determine a normalized histoimage,
 wherein the scatter histoimage is determined based on the normalized histoimage, and wherein the scatter-corrected histoimage is determined based on the normalized histoimage and the scatter histoimage.

13. A method according to claim 12, wherein determining the scatter histoimage comprises:

compressing the normalized histoimage and the linear attenuation coefficient map; and determining the scatter histoimage based on the compressed normalized histoimage and the compressed linear attenuation coefficient map.

14. A method according to claim 13, wherein determining the scatter histoimage comprises inputting the compressed normalized histoimage and the compressed linear attenuation coefficient map to a second trained neural network to generate the scatter histoimage.

15. A non-transitory medium storing program code, the program code executable by at least one processing unit to cause a computing system to:

acquire a computed tomography image of an object;

determine a linear attenuation coefficient map based on the computed tomography image;

acquire positron emission tomography (PET) data of the object;

determine a histoimage of the object based on the PET data;

determine a scatter histoimage based on the histoimage and the linear attenuation coefficient map;

determine a scatter-corrected histoimage based on the histoimage and the scatter histoimage; and input the computed tomography image and the scatter-corrected histoimage to a trained neural network to generate a PET image.

16. A medium according to claim 15, wherein determination of the scatter histoimage comprises:

compressing of the histoimage and the linear attenuation coefficient map; and determination of the scatter histoimage based on the compressed histoimage and the compressed linear attenuation coefficient map.

17. A medium according to claim 16, wherein determination of the scatter histoimage comprises inputting of the compressed histoimage and the compressed linear attenuation coefficient map to a second trained neural network to generate the scatter histoimage.

18. A medium according to claim 16, wherein determination of the scatter-corrected histoimage is based on the compressed histoimage and the scatter histoimage.

19. A medium according to claim 15, wherein determination of the histoimage of the object comprises normalization of the histoimage based on a sensitivity of the scanner to determine a normalized histoimage, wherein the scatter histoimage is determined based on the normalized histoimage, and wherein the scatter-corrected histoimage is determined based on the normalized histoimage and the scatter histoimage.

20. A medium according to claim 19, wherein determination of the scatter histoimage comprises:

compressing of the normalized histoimage and the linear attenuation coefficient map; and inputting of the compressed normalized histoimage and the compressed linear attenuation coefficient map to a second trained neural network to generate the scatter histoimage.

* * * * *